US008101712B2

(12) United States Patent
Keri et al.

(10) Patent No.: US 8,101,712 B2
(45) Date of Patent: Jan. 24, 2012

(54) PURIFICATION PROCESSES FOR ECHINOCANDIN-TYPE COMPOUNDS

(75) Inventors: Vilmos Keri, Debrecen (HU); Andrea Csorvasi, Debrecen (HU); Peter Seress, Debrecen (HU); Zsolt Tomas Suto, Debrecen (HU)

(73) Assignee: TEVA Gyógyszergyár Zártkörúen Múködó Részvénytársaság, Debrecen (HU)

(*) Notice: Subject to any disclaimer, the term of this patent is extended or adjusted under 35 U.S.C. 154(b) by 379 days.

(21) Appl. No.: 11/975,123

(22) Filed: Oct. 16, 2007

(65) Prior Publication Data
US 2008/0108806 A1 May 8, 2008

Related U.S. Application Data

(60) Provisional application No. 60/852,346, filed on Oct. 16, 2006, provisional application No. 60/937,156, filed on Jun. 25, 2007, provisional application No. 60/958,531, filed on Jul. 6, 2007, provisional application No. 60/953,048, filed on Jul. 31, 2007, provisional application No. 60/967,772, filed on Sep. 7, 2007.

(51) Int. Cl.
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |

(52) U.S. Cl. ........................................ 530/323
(58) Field of Classification Search .................. None
See application file for complete search history.

(56) References Cited

U.S. PATENT DOCUMENTS

| 3,966,702 A * | 6/1976 | Carey .................. 530/378 |
| 4,751,322 A * | 6/1988 | Fischer et al. ............... 560/218 |
| 5,021,403 A | 6/1991 | Sesin et al. |
| 5,194,377 A | 3/1993 | Schwartz et al. |
| 5,378,804 A | 1/1995 | Balkovec et al. |
| 5,437,790 A * | 8/1995 | Fyson et al. .................. 210/710 |
| 6,150,364 A * | 11/2000 | Wagner ...................... 514/251 |
| 6,506,726 B1 | 1/2003 | Dobbins et al. |
| 6,590,073 B2 | 7/2003 | Dalder et al. |
| 6,610,822 B2 | 8/2003 | Chandler et al. |
| 6,818,130 B1 * | 11/2004 | Varriale et al. ............... 210/266 |
| 2002/0028916 A1 | 3/2002 | Chandler et al. |

FOREIGN PATENT DOCUMENTS

| WO | WO-02/20618 A1 | 3/2002 |
| WO | WO-03/018615 A1 | 3/2003 |
| WO | WO03018615 A1 * | 3/2003 |

OTHER PUBLICATIONS

Roush et al. Preparative high-performance liquid chromatography of echinocandins. J Chromat. A, 1998. vol. 827, pp. 373-389.*
Fujie et al. FR901469, a Novel Antifungal Antibiotic from an Unidentified Fungus No. 11243. The Journal of Antibiotics. 2000. vol. 53, No. 9, pp. 912-919.*
Morris et al. Pneumocandin Do, a new antifungal agent and potent inhibitor of Pneumocystis carinii. The Journal of Antibiotics, 1994, vol. 47, No. 7, pp. 755-764.*
Schwartz et al. Penumocandins from *Zalerion arboricola*. 1. Discovery and Isolation. The Journal of Antibiotics, 1992. vol. 45, No. 12, pp. 1853-1866.*
Iwamoto et al. WF11899 A, B and C, Novel Antifungal Lipopeptides. I. Taxonomy, fermentation, isolation and physico-chemical properties. The Journal of Antibiotics. 1994. vol. 47. No. 10, pp. 1084-1091.*
Iwamoto et al. WF11899 A, B and C, Novel Antifungal Lipopeptides. II. Biological properties. The Journal of Antibiotics. 1994. vol. 47. No. 10, pp. 1092-1097.*
Snyder, J., Chromatographic Science, 1978, vol. 16, pp. 223-234.
International Search Report, Application No. PCT/US2007/022123, Mar. 13, 2008.
Schwartz, Robert E. et al., "Pneumocandins From *Zalerion arboricola*: I. Discovery and Isolation", The Journal of Antibiotics, Dec. 1992, vol. 45, No. 12, pp. 1853-1866.
Fujie, Akihiko, et al., "FR901469, a Novel Antifungal Antibiotic from an Unidentified Fungus No. 11243, I. Taxonomy, Fermentation, Isolation, Physico-chemical Properties and Biological Properties", The Journal of Antibiotics, Sep. 2000, vol. 53, No. 9, pp. 912-919.

* cited by examiner

*Primary Examiner* — Marcela M Cordero Garcia
(74) *Attorney, Agent, or Firm* — Kenyon & Kenyon LLP

(57) ABSTRACT

The present invention provides a method of preparing and purifying echinocandin-type compounds, such as pneumocandin Bo, WF 11899A, and echinocandin B. These compounds are fermentation products that are used to prepare semi-synthetic products such as the antifungal products Caspofungin, Mycafungin, and Anidulafungin.

21 Claims, 1 Drawing Sheet

PURIFICATION PROCESSES FOR ECHINOCANDIN-TYPE COMPOUNDS

CROSS REFERENCE TO RELATED APPLICATIONS

The present application claims the benefit of the following U.S. Provisional Patent Application Nos. 60/852,346, filed Oct. 16, 2006, 60/937,156, filed Jun. 25, 2007, 60/958,531, filed Jul. 6, 2007, 60/953,048, filed Jul. 31, 2007, and 60/967,772, filed Sep. 7, 2007. The contents of these applications are incorporated herein by reference.

FIELD OF THE INVENTION

The invention encompasses processes for purifying echinocandin-type compounds including pneumocandin $B_0$, WF 11899A and echinocandin B.

BACKGROUND OF THE INVENTION

Pneumocandin $B_0$, WF 11899A and echinocandin B are all members of the echinocandin family, having the general structure:

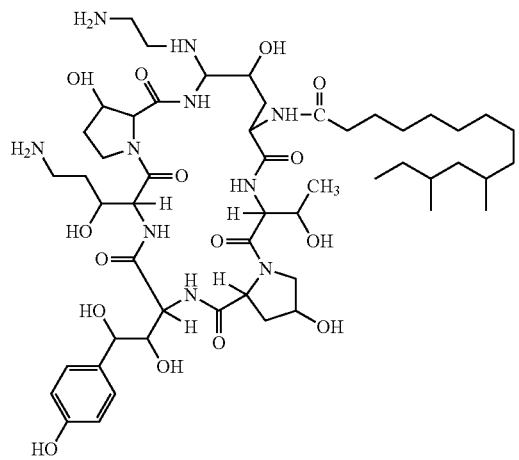

Formula I

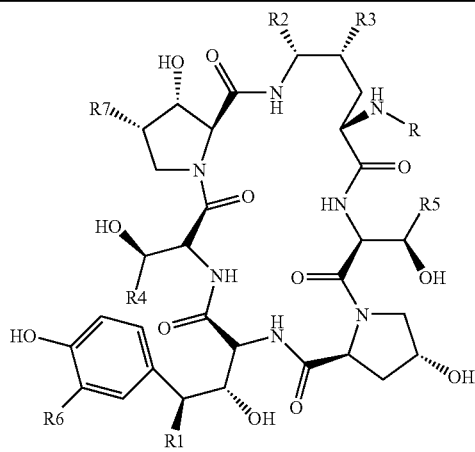

| | R | R1 | R2 | R3 | R4 | R5 | R6 | R7 |
|---|---|---|---|---|---|---|---|---|
| Echinocandin B | Linoleoyl | OH | OH | OH | $CH_3$ | $CH_3$ | H | H |
| Aculeacin Aγ | Palmitoyl | OH | OH | OH | $CH_3$ | $CH_3$ | H | $CH_3$ |
| Mulundocandin | 12-Methyl myristoyl | OH | OH | OH | H | H | H | $CH_3$ |
| Sporiofungin A | 10,12-Dimethyl myristoyl | OH | OH | OH | $CH_2CONH_2$ | H | H | $CH_3$ |
| Pneumocandin $B_0$ | 10,12-Dimethyl myristoyl | OH | OH | OH | $CH_2CONH_2$ | H | H | H |
| WF11899A | Palmitoyl | OH | OH | OH | $CH_2CONH_2$ | $CH_3$ | $OSO_3H$ | $CH_3$ |

They are fermentation products that are used to prepare semi-synthetic products, such as Caspofungin, Mycafungin and Anidulafungin, respectively. They all have antifungal activity.

Caspofungin is the first of a new class termed the echinocandins and works by inhibiting cell wall synthesis. Caspofungin has the chemical name 1-[(4R,5S)-5-[(2-aminoethyl)amino]-N2-(10,12-dimethyl-1-oxotetradecyl)-4-hydroxy-L-ornithine]-5-[(3R)-3-hydroxy-L-ornithine]pneumocandin $B_0$, the CAS Registry Number 179463-17-3, and the following chemical structure (Formula I).

Caspofungin is disclosed in U.S. Pat. No. 5,378,804. Caspofungin is marketed in the form of its diacetate salt in the United States by Merck & Co., Inc. under the trade name CANCIDAS®. CANCIDAS® is administered intravenously for the treatment of infections such as *Aspergillus* and *Candida* and for the prevention of infections found in immunodeficient patients.

Anidulafungin is marketed in the United States by Pfizer under the trade name ERAXIS® and is administered intravenously for the treatment of infections such as *Candida*.

Micafungin is marketed in the form of its sodium salt in the United States by Astellas under the trade name MYCAMINE® and is administered intravenously for the treatment of infections such as *Candida*.

Processes for the preparation of caspofungin involve the use of pneumocandin. Pneumocandin is disclosed in U.S. Pat. No. 5,194,377 and has the following chemical structure:

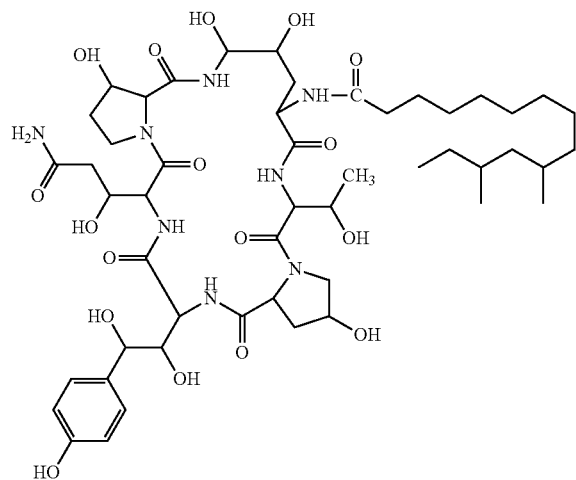

Pneumocandin is prepared by fermentation reactions; where fermentation and mixed broths generally contain a number of related by-products which may be difficult to separate from the desired product. U.S. Pat. No. 6,610,822 describes purification of the echinocandin-type compounds, such as, pneumocandin, WF 11899 and echinocandin B by performing several extraction processes, the first to remove non-polar impurities, the second to remove polar impurities, and then "back-extraction" of the product, optionally, in a combination with chromatographic purification. Hence, U.S. Pat. No. 6,610,822 provides a long and time consuming purification process.

U.S. Pat. No. 5,021,403 describes a purification process of echinocandin-type compounds, such as, pneumocandin, WF 11899 and echinocandin B by performing several chromatographies. Thus, this process isn't suitable for large scale manufacture, isn't economic and is time consuming.

U.S. Pat. Nos. 6,506,726 and 6,590,073 describe the purification of echinocandin-type compounds, especially, of deacylated echinocandin B by chromatography.

The purified substances are echinocandin nuclea, which contain at least one amino group that can be protonated in the presence of an acid. Thus, this process is not suitable for substances that don't have an amine group that is protonated, such as pneumocandin, WF 11899 and echinocandin B.

There is a need in the art for additional processes of purifying echinocandin-type compounds, using techniques that are feasible for use on an industrial scale.

SUMMARY OF THE INVENTION

The invention encompasses processes for purifying an echinocandin-type compound, including pneumocandins. In one embodiment, the invention encompasses a process for purifying an echinocandin-type compound comprising: (a) extracting impurities from a whole broth having an echinocandin-type compound with at least one non polar or weakly polar water-immiscible organic solvent to obtain a first two-phase system comprising an aqueous phase and an organic phase; (b) removing the organic phase to obtain the aqueous phase; (c) extracting the echinocandin-type compound from the aqueous phase with a second water-immiscible organic solvent to obtain a second two-phase system; and (d) recovering the purified echinocandin-type compound from the organic phase of the second two-phase system, wherein the water immiscible organic solvent in steps (a) and (c) are different.

In another embodiment, the invention encompasses a process for purifying an echinocandin-type compounds comprising crystallizing echinocandin-type compounds using at least one anti-solvent.

In yet another embodiment, the invention encompasses a process for purifying an echinocandin-type compound comprising: (a) extracting impurities from a whole broth having an echinocandin-type compound with at least one non polar or weakly polar water-immiscible organic solvent to obtain a first two-phase system comprising an aqueous phase and an organic phase; (b) removing the organic phase to obtain the aqueous phase; (c) extracting the echinocandin-type compound from the aqueous phase with a second water-immiscible organic solvent to obtain a second two-phase system; (d) recovering the echinocandin-type compound; and (e) crystallizing the recovered echinocandin-type compound using at least one anti-solvent, wherein the water-immiscible organic solvent in steps (a) and (c) are different.

In one embodiment, the invention encompasses a process for purifying an echinocandin-type compound comprising, combining echinocandin-type compound with at least one anti-solvent and a solid carrier.

In another embodiment, the invention encompasses a process for purifying an echinocandin-type compound comprising: (a) extracting the echinocandin-type compound from a fermentation broth or from a filtered mycelium obtained from a fermentation broth with a water-immiscible organic solvent to obtain a two-phase system comprising an aqueous phase and an organic phase; (b) recovering the echinocandin-type compound; and (c) combining the recovered echinocandin-type compound with at least one anti-solvent and a solid carrier to obtain a purified echinocandin type compound.

DETAILED DESCRIPTION OF THE INVENTION

Figure 1:
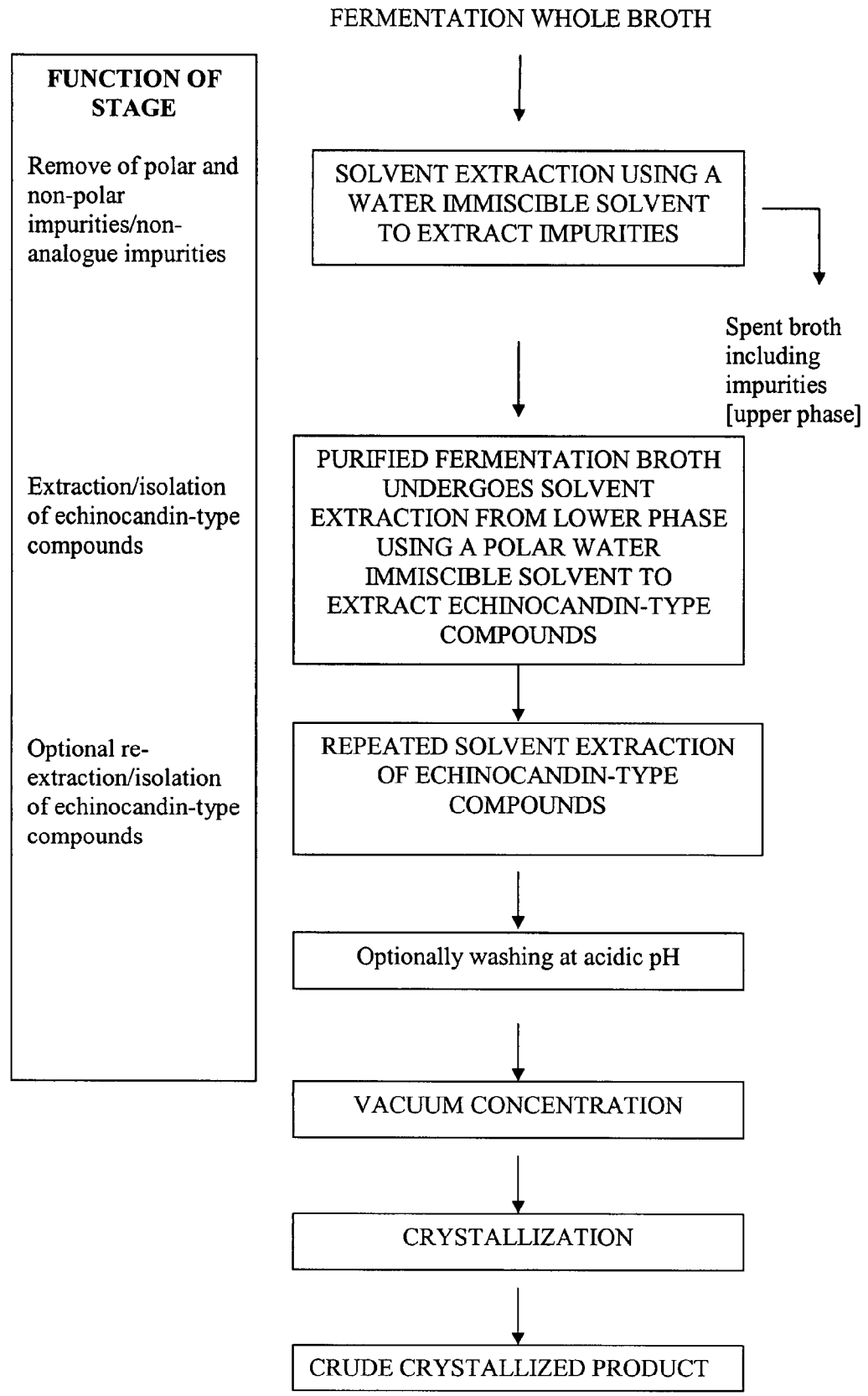
FIG. 1 is a flow chart illustrating one embodiment of the purification process in a step-wise manner.

The invention encompasses processes for purifying pneumocandin or other echinocandin-type compounds. As used herein, unless otherwise defined, the term "Echinocandin-type compounds" refers to compounds having the following general structure including derivatives thereof:

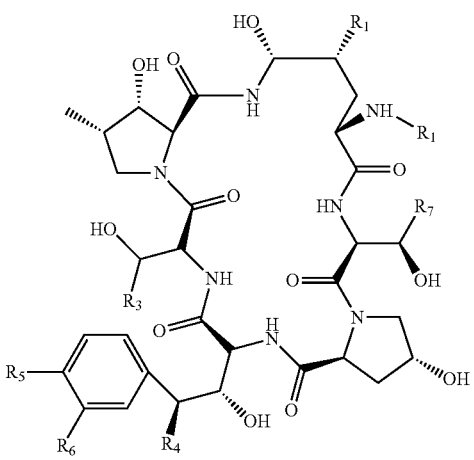

wherein R is a hydrogen or —C(O)R'; R' is an alkyl group, an alkenyl group, an alkynyl group, an aryl group, or heteroaryl group having attached thereon at least one amino group that can be protonated in the presence of an acid; $R_1$ is —H or —OH; $R_2$ is —H or —CH$_3$; $R_3$ is —H, CH$_3$, —CH$_2$CONH$_2$ or —CH$_2$CH$_2$NH$_2$; $R_4$ is —H or —OH; $R_5$ is —OH, —OPO$_3$H$_2$, or —OSO$_3$H; $R_6$ is —H or —OSO$_3$H, and $R_7$ is —H or —CH$_3$.

Preferably, R is linoleoyl, 10,12-dimethyl myristoyl, or palmitoyl. Preferably, $R_1$, $R_4$ and $R_5$ are OH. Preferably, $R_3$ is either Me, or CH$_2$CONH$_2$.

Preferably when R is linoleoyl, $R_1$, and $R_4$ are OH, $R_3$ and $R_7$ are Me, and $R_6$ is H, i.e., the compound is echinocandin B.

Preferably, when R is 10,12-dimethyl myristoyl, $R_1$, and $R_4$ are OH, $R_3$ is CH$_2$CONH$_2$, $R_5$ is OH, and $R_6$ and $R_7$ are H, i.e., the compound is pneumocandin B$_0$.

Preferably, when R is palmitoyl, $R_1$, and $R_4$ are OH, $R_3$ is CH$_2$CONH$_2$, $R_5$ is OH, $R_6$ is OSO$_3$H, and $R_7$ is CH$_3$, i.e., the compound is WF11899A.

Preferably, Echinocandin-type compounds are pneumocandin B$_0$, WF-11899, and echinocandin. These products are not highly soluble in conventional solvents, such as esters, lower alcohols and water. Thus they are difficult to purify by conventional extractions. Therefore, known processes for purification of them are usually complicated and inefficient, especially when handling large amounts of these compounds.

The present invention offers processes for purifying Echinocandin-type compounds, which are suitable for any scale, including industrial scale. These processes of the present invention are simple in that the process steps are uncomplicated, easily scalable to an industrial scale process, and economical while providing echinocandin type compounds of a purity which is sufficient for further processing to obtain an active pharmaceutical ingredient such as for example the antifungals caspofungin, anidulafungin, and micafungin. The first process of the present invention use the low solubility characteristic of the Echinocandin-type compounds.

As used herein, unless mentioned otherwise, the term "water immiscible solvent" refers to a solvent or mixture of solvents that when mixed with water does not form a single mixture but forms an at least two phase system. In contrast, a "water miscible solvent" refers to a solvent or mixture of solvents that when mixed with water forms a single solution phase.

As used herein, unless mentioned otherwise, the term "solid carrier" refers to a material (compound) that is inert and remains undissolved in the process solvents but is capable of forming a mixture with the compound(s).

As used herein unless mentioned otherwise, the term "non-polar" refers to organic solvents having polarity index of about 0 to about 2.4. Examples for such solvents are toluene, heptane, hexane, octane and cyclohexane.

As used herein, unless mentioned otherwise, the term "weakly-polar" refers to organic solvents having polarity index of about 2.4 to about 5.1, excluding alcoholic organic solvents. Examples for such solvents are methyl ethyl ketone, acetone, diisopropyl ether, dibutyl ether, isobutyl acetate, n-propyl acetate, ethyl acetate, dichloromethane, and isopropyl acetate. The polarity index can be measured according to Synder, J. Chromatographic science 16, 223-234 (1978).

In one embodiment, the invention encompasses a process for purifying an echinocandin-type compound comprising: (a) extracting impurities from a whole broth having an echinocandin-type compound with at least one non polar or weakly polar water-immiscible organic solvent to obtain a first two-phase system comprising an aqueous phase and an organic phase; (b) removing the organic phase to obtain the aqueous phase; (c) extracting the echinocandin-type compound from the aqueous phase with a second water-immiscible organic solvent to obtain a second two-phase system; and (d) recovering the purified echinocandin-type compound, wherein the water-immiscible organic solvents in steps (a) and (c) are different.

Where the echinocandin-type compound is pneumocandin B$_0$, the starting unpurified pneumocandin (such as pneumocandin in a fermentation broth) may be prepared, for example, by the process described in U.S. Pat. No. 6,610,822.

Preferably, the echinocandin-type compound is present in the whole broth in a concentration of about 0.2 to about 15 g/L, more preferably, of about 0.2 to about 8 g/L. This concentration of the echinocandin-type compound in the fermentation broth may be determined by HPLC analysis.

In the process of the present invention, the fermentation broth having the echinocandin-type compound is combined with the non-polar or weakly polar water immiscible organic solvent to obtain the first two-phase system. Typically, the two-phase system comprises impurities, such as vegetable oils, amino acids, and small molecular size proteins in the non-polar or weakly polar water-immiscible organic phase and the echinocandin-type compound and the mycelium in the aqueous phase, which is the aqueous medium of the fermentation broth. Thus, in some embodiments, the aqueous phase may also contain insoluble particles.

Therefore, suitable non-polar or weakly polar water-immiscible organic solvents include solvents in which the echinocandin-type compound has low solubility. Preferably, the non-polar or weakly polar water-immiscible organic solvents include, but are not limited to, $C_{5-8}$ aliphatic alkanes, $C_{6-8}$ aromatic hydrocarbons, $C_{4-8}$ ethers, and $C_{3-6}$ esters. Preferably, the $C_{5-8}$ aliphatic alkane is heptane, hexane, octane or cyclohexane. Preferably, the $C_{6-8}$ aromatic hydrocarbon is toluene. Preferably, the $C_{4-8}$ ether is diethyl ether, diisopropyl ether or dibutyl ether. Preferably, the $C_{3-6}$ ester is iso-butyl acetate, n-butyl acetate, n-propyl acetate, isopropyl acetate or ethyl acetate. Most preferably, the non-polar or weakly polar water-immiscible organic solvent is iso-butyl acetate, n-butyl acetate, n-propyl acetate, isopropyl acetate or ethyl acetate.

In the process of the present invention, the amount of the non-polar or weakly polar water-immiscible organic solvent that is used to obtain a first two phase system may be from about 5% to about 90% by volume of the whole broth, depending on the efficiency of the separation of the two phases. If there is efficient phase separation, 5-25% is typically sufficient. However, if there is non-optimal phase separation, 50-90% should be used. Preferably, the amount of water immiscible solvent used is from about 10% to about 50%, more preferably from about 30% to about 50%, most preferably about 50% by volume of the whole broth.

The extraction provides a purified fermentation broth, which is the aqueous phase of step (b). This phase is usually purified enough to continue the extraction process with only one additional extraction step.

The aqueous phase of step (b) is then extracted with a second water-immiscible solvent, to remove the echinocandin-type compound from the aqueous phase. This extraction provides the second two-phase system that comprises the echinocandin-type compound in the water-immiscible organic phase, which is preferably a polar organic phase obtained with extraction with an alcohol and referred to as organic phase, and the mycelium and substances that are not soluble in the organic phase remain in the aqueous phase. Examples for substances that are not soluble in a polar organic phase are several amino acids and amino acid salts, several organic acids and organic acid salts, enzymes, and proteins.

A suitable second water-immiscible organic solvent in step (c) is one having high affinity for echinocandin-type compound. Preferably, the second water-immiscible organic solvent is an alcohol, more preferably a $C_{4-6}$ alcohol, even more preferably a $C_{4-5}$ alcohol, most preferably, isobutanol or n-butanol.

The extraction in step (c) can be repeated to further increase the yield of the echinocandin-type compound in the organic phase. In a preferred embodiment of the present invention the extraction step (c) is repeated.

The echinocandin-type compound is then recovered from the organic phase by any method known in the art, such as evaporating the solvent. The recovery provides a concentrate of the organic phase having the echinocandin-type compound. The concentrate can be a concentrated solution or an oily residue of the echinocandin-type compound, referred herein as concentrated residue.

The obtained concentrated residue can then be further purified by crystallizing the echinocandin-type compound using at least one anti-solvent.

In one embodiment, the present invention provides a process for purifying an echinocandin-type compounds comprising crystallizing echinocandin-type compounds using at least one anti-solvent.

The crystallization comprises admixing the echinocandin-type compound with an anti-solvent to precipitate the echinocandin-type compound. Preferably, the anti-solvent is added to the echinocandin-type compound.

The starting echinocandin-type compounds are, preferably, obtained from extractions of the fermentation broth. The extractions can be done, for example by the process disclosed herein or by any other method known to a skilled artisan.

The starting echinocandin-type compounds can be in a form of a concentrated residue, obtained by the above described process.

As used herein, the term anti-solvent refers to a liquid that is added to a mixture of a solvent and a solid to reduce the solubility of the solid in the solvent.

A suitable anti-solvent causes precipitation of the echinocandin-type compound. Therefore, a suitable anti-solvent is such where the echinocandin-type compound has low solubility. Preferably, suitable anti-solvents include, but are not limited to ethyl acetate, isobutyl acetate, isopropyl acetate, acetone, acetonitrile (ACN), mixtures of acetonitrile with ethylacetate and iso-butylacetate, and mixtures of acetonitrile with iso-butylacetate. Most preferred anti-solvents are isobutyl acetate, n-butyl acetate, tert-butyl acetate, acetonitrile, acetone or isopropyl acetate, and even most preferably, acetonitrile. Preferably, the amount of anti-solvent is added in a ratio of at least 2:1 of anti-solvent:ester, more preferably of about 5:1 to about 2:1, even more preferably of about 3:1 to about 2:1 v/v, respectively.

In a preferred embodiment the anti-solvent is acetonitrile and is present in an amount such that the acetonitrile:ester ratio is at least about 2:1 v/v, respectively. In another preferred embodiment the anti-solvent is acetone and is present in an amount such that the acetone:ester ratio is at least about 2:1 v/v, respectively.

In some embodiments, where the anti-solvent is ethylacetate or isobutyl acetate, the precipitation also includes a cooling step or the addition of a second anti-solvent, such as ACN or acetone, to induce precipitation. Such cooling step may be cooling the mixture of the concentrated residue and the anti-solvent to a temperature of about 5° C. to about −20° C., more preferably of about 5° C. to about 0° C.

In other embodiment, for example, when the anti-solvent is ACN or acetone, the precipitation further comprises cooling to a temperature of about 5° C. to about −20° C., more preferably of about 5° C. to about 0° C., to increase the yield of the precipitated product.

The precipitation provides a suspension, which may be maintained at such temperature for a sufficient period of time to increase the yield of the precipitated product. Preferably, the suspension is maintained for at least about 15 minutes, more preferably for about 10 hours to about 24 hours, most preferably for about 20 hours.

In another process of the invention a solid carrier is used in the purification process, thereby eliminating the first extraction step where impurities are extracted, as for example is needed in the process described above. In addition, a smaller amount of solvents is required in the extraction step(s), and also in the crystallization step, making the process very attractive, especially for large scale manufacture.

This process comprises the steps of (a) extracting the echinocandin-type compound from the fermentation broth or from a filtered mycelium obtained from a fermentation broth with a water-immiscible organic solvent to obtain a two-phase system having an aqueous phase and an organic phase; (b) recovering the echinocandin-type compound; and (c) combining the recovered echinocandin-type compound with at least one anti-solvent and a solid carrier to obtain a purified echinocandin type compound.

Initially, the fermentation broth is combined with a water-immiscible organic solvent to obtain a two-phase system. The water-immiscible organic solvent is as described before, preferably the water-immiscible organic solvent is a water-immiscible alcohol. In a preferred embodiment, the extraction is carried out at a pH of about 2 to about 8, more preferably, at about 5 to about 7. When extracting at acidic pH, such as pH 2 to about 4, the extraction is preferably carried out while cooling and after first cooling the fermentation broth and the polar water-immiscible solvent to avoid decomposition of the product. Preferably, cooling is to a temperature of about 0° C. to 10° C., more preferably of about 0° C. to about 5° C. Typically, the pH is adjusted to a range of about 2 to about 8 by addition of a base or an acid, depending on the pH of the fermentation broth. Suitable bases are, for example, ammonium bases, such as ammonium hydroxide, or diluted aqueous solutions of alkali base, such as sodium hydroxide. Suitable acids are, for example, acetic acids or diluted aqueous solutions of sulfuric acids.

The extraction step can be repeated to increase the yield of the echinocandin-type compound in the second water-immiscible organic phase. Preferably, the extraction is repeated to about 2-4 extractions, more preferably a total of 3 extractions in this extraction step is preferred.

The echinocandin-type compound is then recovered from the organic phase by any method known in the art, such as evaporating the solvent. The recovery provides a concentrate of the organic phase having the echinocandin-type compound. The concentrate can be a concentrated solution or an oily residue of the echinocandin-type compound referred herein as crude concentrated residue.

This crude concentrated residue of the echinocandin-type compound may be obtained by removing the solvent almost to dryness to obtain a concentrate. The removal of the water-immiscible organic solvent can be repeated several times by adding a non-polar or weakly polar water immiscible organic solvent, such as isobutyl acetate, and evaporating the solvents, wherein the non-polar or weakly polar water immiscible organic solvent is different from the water-immiscible solvent in step (a) of the above process.

Optionally, the process comprises an additional washing step of the obtained concentrate, prior to crystallizing the echinocandin-type compound by combining it with an anti-solvent and a solid carrier as in step c). This washing step comprises combining the obtained concentrate with water. In a preferred embodiment, the washing comprises two steps, one using water having a pH of about 4 to about 6.5, preferably of about 4 to about 4.5, and a second, using water having a pH of about 4 to about 6.5, preferably, of about 6 to about 6.5. In addition, when cooling of the obtained concentrate is conducted, for example to about 5° C., water having a pH of less than 4 can be used, for example water having a pH of about 3. The washings can eliminate approximately about 20 to about 50% by weight of solid residues that originated from the fermentation broth and which may be present in the concentrate.

In addition, the concentrate can be treated with active charcoal prior to crystallizing the echinocandin-type compound by combining it with an anti-solvent and a solid carrier as in step c). This treatment comprises mixing active charcoal and the concentrate and then filtering the active charcoal.

The obtained concentrate can then be further purified by combining it with at least one anti-solvent and a solid carrier to obtain a purified echinocandin-type compound.

In one embodiment, the invention encompasses a process for purifying an echinocandin-type compound comprising, combining echinocandin-type compound with at least one anti-solvent and a solid carrier. Preferably, the anti-solvent and the solid carrier are added to the echinocandin-type compound.

The starting echinocandin-type compounds are, preferably, obtained from extractions of the fermentation broth. The extractions can be done, for example by the processes disclosed herein or by any other method known to a skilled artisan.

The starting echinocandin-type compounds can be in a form of a concentrated residue, obtained by the above described processes.

The precipitation of the echinocandin-type compound occurs on the solid carrier, thus the echinocandin-type compound is absorbed on the solid carrier and consequently separated from impurities that are still present in the concentrate obtained in the previous process steps. In precipitating the substance of interest with an anti-solvent, when a smaller volume of anti-solvent is used a high purity of the precipitated substance is obtained, but this smaller volume of anti-solvent also complicates the filtration thereof. The solid carrier facilitates filtration of the otherwise hard to filter precipitated substance. Suitable solid carriers include, but are not limited to active charcoal, diatomaceous earth, wheat meal, corn starch, potato starch, bentonite, perlite, avicel, hydrophobic perlite, active lignite meals, carbons, cellulose products and any other solids, which can be suspended in the solvent solution of the process of the present invention.

In this step of the process, a mixture is prepared by combining the solid carrier and the concentrate obtained in the previous step. The mixture is then combined with an anti-solvent. Preferably, a suitable anti-solvent is as described before in addition to isopropyl acetate and isobutyl acetate. Typically, after the addition of the anti-solvent, a suspension is obtained.

The suspension is then filtered, to remove the solid carrier and the absorbed product.

The process further comprises suspending the filtered solid carrier and the absorbed product to remove the traces of mother liquor. The solvent used for creating the suspension can be a single solvent, such as ACN or acetone or a mixture of two solvents, both in which the echinocandin-type compound possesses low solubility. When a mixture of two solvents is used, the first solvent is one in which the impurities are soluble, such as isobutyl acetate, isopropyl acetate and ethyl acetate, octane, and the second is either acetonitrile or acetone.

Further, the product and the solid carrier may be recovered from the suspension by any method known to a skilled artisan, such as for example by filtration and the subsequent drying the filtered solid. Preferably, the product can be separated from the solid carrier by combining the complex of the solid carrier and the echinocandin type compound with a solvent in which the product is soluble, as for example in alcohols, e.g. methanol, ethanol, n-propanol, iso-propanol, n-butanol, iso-butanol, in DMF or DMSO. The solid carrier is then filtered to obtain the purified product. The filtrate containing the purified product can then be further purified by any known precipitation or chromatography methods.

The above purified echinocandin-type compound can be further used to prepare synthetic products, such as caspofungin, anidulafungin or mycafungin.

Having described the invention with reference to certain preferred embodiments, other embodiments will become apparent to one skilled in the art from consideration of the specification. The invention is further defined by reference to the following examples describing in detail the processes of the invention. Although the examples focus on pneumocandin $B_0$, WF 11899A and echinocandin B, one of ordinary skill in the art would recognize that the processes can be adapted with little or no experimentation to purify other natural products in the echinocandin family. It will also be apparent to those skilled in the art that many modifications, both to materials and methods, may be practiced without departing from the scope of the invention.

EXAMPLES

Example 1

Step a: Purification 1 kg of fermentation broth containing pneumocandin $B_0$ was combined with 0.5 liter of iso-butyl acetate to form a two-phase system. The two phases were separated with a centrifuge. The iso-butyl acetate phase was removed. All of the pneumocandin $B_0$ remained in the purified fermentation broth.

The purified fermentation broth was then extracted with 500 ml of iso-butanol. The extraction was then repeated with an additional 500 ml of iso-butanol. The two resulting iso-butanol phases were combined to obtain an iso-butanol phase of 1090 ml. The overall yield of purification and extractions was approximately 100%.

Step b: Crystallization

The iso-butanol phase was divided into five 200-ml portions. Pneumocandin $B_0$ crude was crystallized from each of the portions by the following processes.

i) One 200 ml portion was concentrated to 3.5 g under reduced pressure. 17.5 ml of iso-butylacetate was then added. The resulting solution was then cooled to 0-5° C. The solution was left standing for approximately 20 hours, during which crystallization occurred. The resulting crystals were then filtered from the solution and dried. The yield of crude product was 37%.

ii) Another 200 ml portion was concentrated to 3.5 g under reduced pressure. 17.5 ml of acetonitrile was then added. The resulting solution was then cooled to 0-5° C. The solution was left standing for approximately 20 hours, during which crystallization occurred. The resulting crystals were then filtered from the solution and dried. The yield of crude product was 75%.

iii) Another 200 ml portion was concentrated to 3.5 g under reduced pressure. 17.5 ml of ethyl acetate was then added. The resulting solution was then cooled to 0-5° C. The solution was left standing for approximately 20 hours, during which crystallization occurred. The resulting crystals were then filtered from the solution and dried. The yield of crude product was 84%.

iv) Another 200 ml portion was concentrated to 3.5 g under reduced pressure. 3.5 ml of butyl acetate and 10.5 ml of acetonitrile were then added. The resulting solution was then cooled to 0-5° C. The solution was left standing for approximately 20 hours, during which crystallization occurred. The resulting crystals were then filtered from the solution and dried. The yield of crude product was 83%.

v) One 200 ml portion was concentrated to 3.5 g under reduced pressure. 3.5 ml of ethyl acetate and 10.5 ml of acetonitrile were then added. Subsequently, 17.5 ml of iso-butylacetate was then added. The resulting solution was then cooled to 0-5° C. The solution was left standing for approximately 20 hours, during which crystallization occurred. The resulting crystals were then filtered from the solution and dried. The yield of crude product was 74%.

Example 2

Step a: Purification 1 kg of fermentation broth containing pneumocandin $B_0$ was combined with 0.5 liter of n-butylacetate to form a two-phase system. The two phases were separated with a centrifuge. The n-butylacetate phase was removed so that the pneumocandin $B_0$ remained in the purified fermentation broth.

The purified fermentation broth was then extracted with 500 ml of n-butanol. The extraction was then repeated with an additional 500 ml of n-butanol. The two resulting n-butanol phases were combined to obtain an n-butanol phase of 1150 ml.

Step b: Crystallization

The n-butanol phase was concentrated to 18 g under reduced pressure. 18 ml of iso-butylacetate and 54 ml of acetonitrile were then added. The resulting solution was then cooled to 0-5° C. The solution was left standing for approximately 20 hours, during which crystallization occurred. The resulting crystals were then filtered from the solution and dried. The yield of crude product was 64%.

Example 3

Step a: Purification 1 kg of fermentation broth containing pneumocandin $B_0$ was combined with 0.5 liter of n-propylacetate to form a two-phase system. The two phases were separated with a centrifuge. The n-propylacetate phase was removed so that the pneumocandin $B_0$ remained in the purified fermentation broth.

The purified fermentation broth was then extracted with 500 ml of iso-butanol. The extraction was then repeated with an additional 500 ml of iso-butanol. The two resulting n-butanol phases were combined to obtain an iso-butanol phase of 1140 ml.

Step b: Crystallization

The iso-butanol phase was concentrated to 9 g under reduced pressure. 9 ml of iso-butylacetate and 27 ml of acetonitrile were then added. The resulting solution was then cooled to 0-5° C. The solution was left standing for approximately 20 hours, during which crystallization occurred. The resulting crystals were then filtered from the solution and dried. The yield of crude product was greater than 80%.

Example 4

Step a: Purification 1 kg of fermentation broth containing pneumocandin $B_0$ was combined with 0.5 liter of toluene to form a two-phase system. The two phases were separated with a centrifuge. The toluene phase was removed so that the pneumocandin $B_0$ remained in the purified fermentation broth.

The purified fermentation broth was then extracted with 500 ml of iso-butanol. The extraction was then repeated with an additional 500 ml of iso-butanol. The two resulting n-butanol phases were combined to obtain an iso-butanol phase of 1120 ml.

Step b: Crystallization

The iso-butanol phase was concentrated to 12 g under reduced pressure. 12 ml of iso-butylacetate and 36 ml of acetonitrile were then added. The resulting solution was then cooled to 0-5° C. The solution was left standing for approximately 20 hours, during which crystallization occurred. The resulting crystals were then filtered from the solution and dried. The yield of crude product was 52%.

Example 5

Step a: Purification 1 kg of fermentation broth containing pneumocandin $B_0$ was combined with 0.5 liter of hexane to form a two-phase system. The two phases were separated with a centrifuge. The hexane phase was removed so that the pneumocandin $B_0$ remained in the purified fermentation broth.

The purified fermentation broth was then extracted with 500 ml of iso-butanol. The extraction was then repeated with an additional 500 ml of iso-butanol. The two resulting n-butanol phases were combined to obtain an iso-butanol phase of 910 ml.

Step b: Crystallization

The iso-butanol phase was concentrated to 18 g under reduced pressure. 18 ml of iso-butylacetate and 54 ml of acetonitrile were then added. The resulting solution was then cooled to 0-5° C. The solution was left standing for approximately 20 hours, during which crystallization occurred. The resulting crystals were then filtered from the solution and dried. The yield of crude product was 88%.

Example 6

Fermented broth was filtered and the filtered mycelium was split into several parts. Each part of filtered mycelia was suspended in a solvent in a volume of 2 times the mass of filtered mycelium part. After stirring, the mycelia was filtered from the solvent. Each solvent removed impurities. Solvents such as ethyl acetate, hexane, petroleum ether and dichloromethane resulted in purification with a negligible loss. Solvents such as acetone, methanol, ethanol, n-propanol, isopropanol and acetonitrile resulted in purification at a significant loss.

Example 7

Step a 190 kg pneumocandin fermented broth—containing 414.8 g pneumocandin $B_0$—was extracted with 95 L iso-butanol at pH 5.0-7.0. The extraction step was repeated with an additional 95 L isobutanol. The two resulting isobutanol phases were combined to obtain an isobutanol phase of 191 L.

The combined iso-butanol phase was evaporated to volume of 25 L. This concentrate was washed two times with 12.5 L water at pH 4.0-4.5. After acidic washing the concentrate was washed two times with 6 L water at pH 6.0-6.5.

The washed concentrate was clarified with active charcoal of 193 g. After charcoal treatment the concentrate was evaporated to a volume of 4.8 L. 3.6 L of iso-butyl acetate was added to final concentrate and the solution was evaporated again to 4.8 L. This step was repeated.

The getting final concentrate contained 296.7 g pneumocandin $B_0$. Yield was 71.5%.

Step b: Precipitation of Crude Pneumocandin $B_0$ to Different Carriers

1. Diatomaceous earth (the used type was FW-14) of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 87.2 g of crude product—containing 13.88 g pneumocandin $B_0$—was prepared. The yield of precipitation was 89.9%.
2. Wheat meal of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 77.09 g of crude product—containing 8.72 g pneumocandin $B_0$—was prepared. The yield of precipitation was 56.5%.
3. Corn starch of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 80.02 g of crude product—containing 12.63 g pneumocandin $B_0$—was prepared. The yield of precipitation was 81.8%.
4. Potato starch of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 78.31 g of crude product—containing 14.56 g pneumocandin $B_0$—was prepared. The yield of precipitation was 94.3%.
5. Bentonite (the used type was S-100) of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 80.97 g of crude product—containing 11.14 g pneumocandin $B_0$—was prepared. The yield of precipitation was 72.2%.
6. Bentonite (the used type was T2-350) of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 81.14 g of crude product—containing 10.70 g pneumocandin $B_0$—was prepared. The yield of precipitation was 69.3%.
7. Active charcoal of 59.4 g was added to final concentrate of volume 500 ml. 800 ml of acetonitrile was added to the suspension and the mixture was stirred further 1 hour at ambient temperature. The mixture was filtered and the filter cake was suspended with 1000 ml of acetonitrile-isobutyl acetate 1:1 mixture. Filter cake was dried at 40° C. for 12 hour. 109.02 g of crude product—containing 25.44 g pneumocandin $B_0$—was prepared. The yield of precipitation was 82.4%.
8. Perlite (the used type was CP-800) of 19.8 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 47.46 g of crude product—containing 13.54 g pneumocandin $B_0$—was prepared. The yield of precipitation was 87.7%.
9. Avicel (the used type was 200) of 59.4 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 81.65 g of crude product—containing 9.62 g pneumocandin $B_0$—was prepared. The yield of precipitation was 62.3%.
10. Active lignite of 29.7 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 53.56 g of crude product—containing 13.45 g pneumocandin $B_0$—was prepared. The yield of precipitation was 87.1%.
11. Hydrophobic perlite of 19.8 g was added to final concentrate of volume 250 ml. 400 ml of acetonitrile was added to the suspension and the mixture was stirred further 1 hour at ambient temperature. The mixture was filtered and the filter cake was suspended with 500 ml of acetonitrile-isobutyl acetate 1:1 mixture. Filter cake was dried at 40° C. for 12 hour. 43.83 g of crude product—containing 13.43 g pneumocandin $B_0$—was prepared. The yield of precipitation was 86.9%.

Example 8

Step a 100.0 kg WF-11899A diluted fermented broth—containing approx. 36.5 g WF-11899A—was extracted with 100.0 L iso-butanol at pH 5.0-7.0. The extraction step was repeated with an additional 60.0 L iso-butanol. The two resulting iso-butanol phases were combined to obtain an iso-butanol phase of 161.0 L.

The combined iso-butanol phase was evaporated to volume of 12.3 L. This concentrate was washed with 6.0 L water at pH 4.0-4.5. After acidic washing the concentrate was washed with 6.0 L water at pH 6.0-6.5.

The washed concentrate was clarified with active charcoal of 9.1 g. After charcoal treatment the concentrate was divided into two parts. First part (6.9 L) evaporated to volume of 1.3 L. An equal volume (1.3 L) of isobutyl acetate was added to concentrate and the solution was evaporated again to volume of previous step. This step was repeated twice. The weight of the first final concentrate was 740.41 g.

The second part (3.3 L) evaporated to weight of 337.3 g. A volume (300 ml) of isobutyl acetate was added to concentrate and the solution was evaporated again to volume of previous step. This step was repeated twice. The weight of the second final concentrate was 316.07 g.

The obtained final concentrate contained 20.25 g WF-11899A. Yield was 55.5%.

Step b: Precipitation of Crude WF-11899A (FR-901379) to Different Carriers

1. Diatomaceous earth (the used type was FW-14) of 6.0 g and 5.0 ml of isopropyl acetate were added to final concentrate of weight 10 g. 35 ml of acetonitrile was added to the suspension and the mixture was stirred further 5 hour at ambient temperature. The mixture was filtered and the filter cake was suspended with 10 ml of acetonitrile. Filter cake was dried at 40° C. for 12 hours. 10.0 g of crude product—containing 213.1 mg WF-11899A—was prepared. The yield of precipitation was 98.6
2. Diatomaceous earth (the used type was FW-14) of 300.0 g and 178.0 ml of isopropyl acetate were added to final concentrate of weight 336.0 g. 1176 ml of acetonitrile was added to the suspension and the mixture was stirred further 5 hour at ambient temperature. The mixture was filtered and the filter cake was suspended with 336 ml of acetonitrile. Filter cake was dried at 40° C. for 12 hours. 451.6 g of crude product—containing 6.66 g WF-11899A—was prepared. The yield of precipitation was 91.7%.
3. Perlite (the used type was CP-800) of 6.0 g and 5.0 ml of isopropyl acetate were added to final concentrate of weight 10 g. 35 ml of acetonitrile was added to the suspension and the mixture was stirred further 5 hour at ambient temperature. The mixture was filtered and the filter cake was suspended with 10 ml of acetonitrile. Filter cake was dried at 40° C. for 12 hours. 9.61 g of crude product—containing 221.3 mg WF-11899A—was prepared. The yield of precipitation was 98.3%.
4. Avicel (the used type was 200) of 6.0 g and 5.0 ml of isopropyl acetate were added to final concentrate of weight 10 g. 35 ml of acetonitrile was added to the suspension and the mixture was stirred further 5 hour at ambient temperature. The mixture was filtered and the filter cake was suspended with 10 ml of acetonitrile. Filter cake was dried at 40° C. for 12 hours. 9.71 g of crude product—containing 202.4 mg WF-11899A—was prepared. The yield of precipitation was 93.6%.
5. Avicel (the used type was 200) of 400.0 g and 200.0 ml of isopropyl acetate were added to final concentrate of weight 404.0 g. 1414 ml of acetonitrile was added to the suspension and the mixture was stirred further 5 hour at ambient temperature. The mixture was filtered and the filter cake was suspended with 404 ml of acetonitrile. Filter cake was dried at 40° C. for 12 hours. 549.2 g of crude product—containing 8.31 g WF-11899A—was prepared. The yield of precipitation was 95.5%

Example 9

Step a

Echinocandin fermented broth is extracted with half volume of iso-butanol at pH 5.0-7.0. The extraction step is repeated with an additional half volume of iso-butanol. The two resulting iso-butanol phases are combined.

The combined iso-butanol phase is concentrated and washed at acidic and neutral pH. The washed concentrate is clarified with active charcoal. After charcoal treatment the concentrate is evaporated to oily residue. Isobutyl acetate is added to final concentrate and the solution is evaporated again to starting volume. This step is repeated.

Step b: Precipitation of Crude Echinocandin

Diatomaceous earth (the used type was FW-14) is added to final concentrate. Acetonitrile is added to the suspension to precipitate the crude product. The mixture is stirred further 1 hour at ambient temperature. The mixture is filtered and the filter cake is suspended with acetonitrile-isobutyl acetate 1:1 mixture. Filter cake is dried at 40° C. for 12 hour.

Example 10

Separation of Active Substance—Pneumocandin $B_0$—from the Carrier 10 kg of pneumocandin $B_0$ crude product (on diatomaceous earth, assay: 13.07%, HPLC purity 35.7%) containing 1307 g active substance was stirred with 100 L of normal propanol for about 1 hour. Diatomaceous earth was filtered and washed with 10 L normal propanol. The combined propanolic solution (appr. 110 L) was evaporated under reduced pressure to a volume of 11.4 L. 46 L of isopropyl acetate was added to the concentrate and the mixture was cooled to (−)10° C.-(−)20° C. The mixture was stirred for further 16-18 hours at (−)10° C.-(−)20° C. The precipitated material was filtered and washed with 10 L of isopropyl acetate. Pneumocandin $B_0$ was dried at 40° C. for appr. 12 hours. The mass of the product was 4.89 kg. The assay was 26.21%, and the HPLC purity was 41.12. The yield of the step was 98%.

We claim:

1. A process for purifying an echinocandin-type compound comprising:
   (a) extracting an echinocandin-type compound from a fermentation broth or from a filtered mycelium obtained from a fermentation broth, with a water-immiscible organic solvent to obtain a two-phase system comprising an aqueous phase and an organic phase or to obtain a water containing organic phase;
   (b) recovering the echinocandin-type compound;
   (c) combining the recovered echinocandin-type compound with at least one anti-solvent and a solid carrier to obtain a mixture comprising the anti-solvent and the solid carrier to which a purified echinocandin-type compound is absorbed;
   (d) separating the mixture to obtain the solid carrier to which a purified echinocandin-type compound is absorbed; and
   (e) recovering the purified echinocandin-type compound from the separated solid carrier.

2. The process of claim 1, wherein the water-immiscible organic solvent in step (a) is a water-immiscible alcohol.

3. The process of claim 2, wherein the water-immiscible alcohol is a $C_{4-6}$ alcohol.

4. The process of claim 3, wherein the $C_{4-6}$ alcohol is isobutanol or n-butanol.

5. The process of claim 1, wherein the extracting in step (a) is carried out at a pH of about 2 to about 8.

6. The process of claim 5, wherein the pH is about 5 to about 7.

7. The process of claim 5, wherein the pH is at about 2 to about 4 and the extracting is carried out while cooling to a temperature of less than about 10° C.

8. The process of claim 1, wherein the extracting step (a) is repeated.

9. The process of claim 1, further comprising an additional washing step of the recovered echinocandin-type compound, prior to combining the recovered echinocandin-type compound with an anti-solvent and a solid carrier in step (c).

10. The process of claim 9, wherein the washing step comprises combining the recovered echinocandin-type compound with water.

11. The process of claim 10, wherein the washing step comprises two steps, one using water having a pH of about 4 to about 6.5, and a second, using water having a pH of about 4 to about 6.5.

12. The process of claim 11, wherein the first washing comprises washing with water having a pH of about 4 to about 4.5 and the second washing comprises washing with water having a pH of about 6 to about 6.5.

13. The process of claim 1, further comprising a step of treating the recovered echinocandin-type compound with active charcoal prior to combining the recovered echinocandin-type compound with an anti-solvent and a solid carrier as in step (c).

14. The process of claim 1, further comprising the step of crystallizing the echinocandin-type compound comprising combining it with at least one anti-solvent and a solid carrier to obtain a purified echinocandin-type compound.

15. The process of claim 1, wherein the solid carrier is selected from the group consisting of active charcoal, diatomaceous earth, wheat meal, corn starch, potato starch, bentonite, perlite, avicel, hydrophobic perlite, active lignite meals, carbons, and cellulose products.

16. The process of claim 1, wherein the anti-solvent is selected from the group consisting of ethyl acetate, isobutyl acetate, n-butyl acetate, tert-butyl acetate, isopropyl acetate, acetone, acetonitrile (ACN), mixtures of acetonitrile with ethylacetate and with iso-butylacetate, and mixtures of acetonitrile (ACN) with iso-butylacetate.

17. The process of claim 1, wherein recovering the purified echinocandin-type compound comprises filtering the mixture of the echinocandin type compound, the solid carrier and the anti-solvent and suspending the filtered solid carrier to which the echinocandin-type compound is absorbed in a solvent selected from the group consisting of acetonitrile, acetone or a mixture of two organic solvents to obtain the echinocandin-type compound absorbed to the solid carrier.

18. The process of claim 17, wherein the mixture of two organic solvents comprises a first solvent selected from the group consisting of isobutyl acetate, isopropyl acetate, ethyl acetate, octane, and a second solvent selected from the group consisting of acetonitrile or acetone.

19. The process of claim 1, wherein recovering the purified echinocandin-type compound comprises combining the solid carrier to which the echinocandin-type compound is absorbed with a solvent in which the echinocandin-type compound is soluble to obtain the purified echinocandin-type compound separated from the solid carrier.

20. The process of claim 19, wherein the solvent in which the echinocandin-type compound is soluble is selected from the group consisting of methanol, ethanol, n-propanol, iso-propanol, n-butanol, iso-butanol, dimethylformamide (DMF), dimethylsulfoxide (DMSO), a mixture thereof, and a mixture of thereof in water.

21. The process of claim 1, further comprising preparing a synthetic product from the purified echinocandin-type compound comprising the step of converting the purified echinocandin-type compound to caspofungin, anidulafungin or mycafungin.

* * * * *